US011684502B2

(12) United States Patent
Schorer et al.

(10) Patent No.: US 11,684,502 B2
(45) Date of Patent: Jun. 27, 2023

(54) SEGMENTED GASTROINTESTINAL DEVICES AND METHODS OF USE THEREOF

(71) Applicant: GI Dynamics, Inc., Boston, MA (US)

(72) Inventors: Scott Schorer, Duxbury, MA (US); Chris Thompson, Needham, MA (US)

(73) Assignee: GI Dynamics, Inc., Boston, MA (US)

( * ) Notice: Subject to any disclaimer, the term of this patent is extended or adjusted under 35 U.S.C. 154(b) by 490 days.

(21) Appl. No.: 16/632,787

(22) PCT Filed: Jul. 23, 2018

(86) PCT No.: PCT/US2018/043334
§ 371 (c)(1),
(2) Date: Jan. 21, 2020

(87) PCT Pub. No.: WO2019/018854
PCT Pub. Date: Jan. 24, 2019

(65) Prior Publication Data
US 2020/0206007 A1   Jul. 2, 2020

Related U.S. Application Data

(60) Provisional application No. 62/535,395, filed on Jul. 21, 2017.

(51) Int. Cl.
*A61F 5/00*   (2006.01)
*A61L 27/18*   (2006.01)

(52) U.S. Cl.
CPC .............. *A61F 5/0076* (2013.01); *A61L 27/18* (2013.01)

(58) Field of Classification Search
CPC ................ A61J 15/0015; A61J 15/0019; A61J 15/0023; A61J 15/0026; A61J 15/003; A61J 15/0034; A61J 15/0038; A61J 15/0042; A61J 15/0046; A61J 15/0049; A61J 15/0053; A61J 15/0057; A61J 15/0061; A61J 15/0065; A61J 15/0069; A61J 15/0073; A61J 15/0076; A61J 15/008; A61J 15/0084; A61J 15/0088; A61J 15/0092; A61J 15/0096; A61M 2039/0255; A61F 5/0013; A61F 5/0036; A61F 5/0076
See application file for complete search history.

(56) References Cited

U.S. PATENT DOCUMENTS

| | | |
|---|---|---|
| 5,820,584 A | 10/1998 | Crabb |
| 6,514,286 B1 | 2/2003 | Leatherbury et al. |
| 7,025,791 B2 | 4/2006 | Levine et al. |
| 7,122,058 B2 | 10/2006 | Levine et al. |

(Continued)

FOREIGN PATENT DOCUMENTS

| | | |
|---|---|---|
| WO | WO-2005/060869 A1 | 7/2005 |
| WO | WO-2005/060882 A1 | 7/2005 |

(Continued)

*Primary Examiner* — Susan S Su
*Assistant Examiner* — Ted Yang
(74) *Attorney, Agent, or Firm* — Clark & Elbing LLP (57) ABSTRACT

A gastrointestinal device and methods of use thereof for the treatment of metabolic disorders is provided. The gastrointestinal device features disintegrable sleeve configured to fit within a patient's duodenum and to carry fluid (e.g., liquid or semisolid material, for example, chyme and digestive secretions) from its proximal end to its distal end.

19 Claims, 2 Drawing Sheets

(56) References Cited

U.S. PATENT DOCUMENTS

| | | |
|---|---|---|
| 7,267,694 B2 | 9/2007 | Levine et al. |
| 7,329,285 B2 | 2/2008 | Levine et al. |
| 7,347,875 B2 | 3/2008 | Levine et al. |
| 7,361,180 B2 | 4/2008 | Saadat et al. |
| 7,416,554 B2 | 8/2008 | Lam et al. |
| 7,476,256 B2 | 1/2009 | Meade et al. |
| 7,608,114 B2 | 10/2009 | Levine et al. |
| 7,608,144 B2 | 10/2009 | Voutsas et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,736,379 B2 | 6/2010 | Ewers et al. |
| 7,758,535 B2 | 7/2010 | Levine et al. |
| 7,766,973 B2 | 8/2010 | Levine et al. |
| 7,771,382 B2 | 8/2010 | Levine et al. |
| 7,815,589 B2 | 10/2010 | Meade et al. |
| 7,815,591 B2 | 10/2010 | Levine et al. |
| 7,819,836 B2 | 10/2010 | Levine et al. |
| 7,837,643 B2 | 11/2010 | Levine et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,137,301 B2 | 3/2012 | Levine et al. |
| 8,162,871 B2 | 4/2012 | Levine et al. |
| 8,303,669 B2 | 11/2012 | Meade et al. |
| 8,425,451 B2 | 4/2013 | Levine et al. |
| 8,628,583 B2 | 1/2014 | Meade et al. |
| 8,740,940 B2 | 6/2014 | Maahs et al. |
| 8,771,219 B2 | 7/2014 | Meade et al. |
| 8,834,405 B2 | 9/2014 | Meade et al. |
| 8,870,806 B2 | 10/2014 | Levine et al. |
| 8,920,358 B2 | 12/2014 | Levine et al. |
| 9,084,669 B2 | 7/2015 | Meade et al. |
| 9,095,416 B2 | 8/2015 | Meade et al. |
| 9,155,609 B2 | 10/2015 | Levine et al. |
| 9,237,944 B2 | 1/2016 | Meade et al. |
| 9,278,020 B2 | 3/2016 | Levine et al. |
| 9,456,917 B2 | 10/2016 | Zeiner et al. |
| 9,545,255 B2 | 1/2017 | Cox et al. |
| 9,572,565 B2 | 2/2017 | Ewers et al. |
| 9,585,783 B2 | 3/2017 | Meade et al. |
| 9,744,061 B2 | 8/2017 | Meade et al. |
| 9,750,596 B2 | 9/2017 | Levine et al. |
| 11,026,826 B2 | 6/2021 | Dicesare et al. |
| 2004/0039350 A1* | 2/2004 | McKittrick ......... A61J 15/0003 604/270 |
| 2004/0092892 A1* | 5/2004 | Kagan ................ A61B 17/0401 604/270 |
| 2006/0206063 A1 | 9/2006 | Kagan et al. |
| 2007/0010866 A1* | 1/2007 | Dann ............... A61B 17/00234 623/1.11 |
| 2007/0032879 A1* | 2/2007 | Levine ...................... A61F 2/04 623/1.36 |
| 2009/0182424 A1* | 7/2009 | Marco .................. A61F 5/0036 606/198 |
| 2011/0004230 A1 | 1/2011 | Levine et al. |
| 2013/0253410 A1 | 9/2013 | Levine et al. |
| 2016/0135976 A1 | 5/2016 | Levine et al. |
| 2016/0206458 A1 | 7/2016 | Hanlon et al. |
| 2017/0172779 A1 | 6/2017 | Meade et al. |
| 2019/0038445 A1 | 2/2019 | Levine et al. |

FOREIGN PATENT DOCUMENTS

| | | |
|---|---|---|
| WO | WO-2006/034062 A1 | 3/2006 |
| WO | WO-2006/078781 A1 | 7/2006 |
| WO | WO-2006/078927 A1 | 7/2006 |
| WO | WO-2006/133311 A2 | 12/2006 |
| WO | WO-2009/036244 A1 | 3/2009 |
| WO | WO-2016/033011 A1 | 3/2016 |
| WO | WO-2017/132676 A1 | 8/2017 |

* cited by examiner

FIG. 1A

Erodible portions → 4, 3, 2, 1

SEGMENTED GASTROINTESTINAL DEVICES AND METHODS OF USE THEREOF

BACKGROUND OF THE INVENTION

According to the Center for Disease Control, 9.3% of the population of the United States has been diagnosed with type 2 diabetes or is predicted to develop type 2 diabetes, over half of whom are clinically obese. Type 2 diabetes and obesity can be broadly characterized as metabolic disorders, which often lead to life-threatening co-morbidities including non-alcoholic steatohepatitis (NASH), non-alcoholic fatty liver disease (NAFLD), hypertension, coronary artery disease, hypercholesteremia, sleep apnea, and pulmonary hypertension.

Patients suffering from metabolic diseases typically have an aberrant physiological response to ingested food after a meal. In particular, inadequate secretion of insulin has been associated with development of metabolic disorders such as type 2 diabetes. This blunted insulin response is caused by a loss or reduction of the "incretin effect," the gut-dependent secretion of incretins (e.g., hormones such as glucagon-like peptide-1 (GLP-1) and glucose-dependent insulinotropic polypeptide (GIP)). Thus, the modulation of signaling pathways in the gastrointestinal tract is emerging as a promising approach for treating metabolic disorders, such as type 2 diabetes, obesity, and related comorbidities.

Many conventional treatments involve surgical modification of gastrointestinal anatomy. Such procedures include, for example, gastric remodeling and gastric bypass. Unfortunately, the morbidity rate for surgical procedures is alarmingly high, with 11% of cases requiring surgical intervention for correction. Early small bowel obstruction has been estimated to occur at a rate of between 2-6% in these surgeries, and mortality rates are reported to be approximately 0.5-1.5%, and are most likely much higher. While invasive surgery seems to be effective when successfully performed, the associated complication rates are unacceptably high. Laparoscopic techniques adapted to these procedures provide fewer surgical complications but continue to expose these patients to high operative risk in addition to requiring an enormous level of skill by the surgeon.

Thus, there is a need in the field increasing patient safety and reducing discomfort when using implantable gastric devices as a procedure for the treatment of metabolic disorders, such as type 2 diabetes, NASH, NAFLD, obesity, and related comorbidities thereof, by modulating physiological responses to ingested food.

SUMMARY OF THE INVENTION

The present invention provides a gastrointestinal device and methods for the treatment of metabolic disorders. In one aspect, the invention features a gastrointestinal device having a disintegrable sleeve configured to fit within a patient's gastrointestinal system, e.g., the antrum or duodenum, and to carry fluid (e.g., liquid or semisolid material, for example, chyme and digestive secretions) from its proximal end to its distal end, wherein the disintegrable sleeve contains a plurality of non-erodible segments connected by erodible portions, such that, upon erosion of the erodible portions, the non-erodible segments can separate.

In some embodiments, the plurality of non-erodible segments are aligned along a longitudinal axis. In some embodiments, each of the plurality of non-erodible segments is annular. In some embodiments, the one or more erodible portions are configured to erode in a distal-to-proximal direction. In some embodiments, the one or more erodible portions are strips that run perpendicularly to the longitudinally aligned non-erodible segments. In other embodiments, the one or more erodible portions are strips that run substantially non-perpendicularly to the longitudinally aligned non-erodible segments.

In some embodiments, the one or more erodible portions have a longitudinal width that is no more than 10% that of the non-erodible segments of the sleeve (e.g., no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5%, no more than 6%, no more than 7%, no more than 8%, no more than 9%, or no more than 10%). In some embodiments, the one or more erodible portions have a thickness that is at least 5% less than the non-erodible segments of the sleeve (e.g., at least 5% less, at least 6% less, at least 7% less, at least 8% less, at least 9% less, at least 10% less, at least 11% less, at least 12% less, at least 13% less, at least 14% less, at least 15% less, at least 16% less, at least 17% less, at least 18% less, at least 19% less, at least 20% less, at least 30% less, at least 40% less, at least 50% less, at least 60% less, at least 70% less, at least 80% less, or at least 90% less, e.g., between 5% and 10% less, between 10% less and 20% less, between 20% less and 30% less, between 30% less and 40% less, between 40% less and 50% less, between 50% less and 60% less, between 60% less and 70% less, between 70% less and 80% less, or between 80% less and 90% less). In some embodiments, the one or more erodible portions are made poly(lactic acid) (PLA), poly (glycolic acid) (PGA), poly(L-lactic acid) (PLLA), poly-DL-lactide (PDLLA), poly-LD-lactide (PLDLA), diolamine, trimethylene carbonate, caprolactone, dioxanone, polydioxanone (PDO), or copolymers thereof.

In one embodiment, the one or more erodible portions are made from PGA.

In some embodiments, the non-erodible segments of the sleeve are made from a polymeric material. In some embodiments, the non-erodible segments of the sleeve are made from polytetrafluoroethylene (PTFE), expanded polytetrafluoroethylene (ePTFE), fluorinated ethylene propylene (FEP), perfluoroalkoxy (PFA), ethylene tetrafluoroethylene (EFTE), or polyvinylidene fluoride (PVDF).

In one embodiment, the non-erodible segments of the sleeve are made from PTFE.

In further embodiments, the gastrointestinal device of the invention contains an anchoring system for securing the sleeve to a patient's gastrointestinal tract. In some embodiments, the sleeve contains an eversion resistant element. In some embodiments, the diameter of the sleeve is substantially constant along its length and may have a length of at least about 30 cm (e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm). In some embodiments, the diameter of the sleeve is substantially constant along its length and may have a length of no more than 150 cm (e.g., no more than 140 cm, no more than 130 cm, no more than 120 cm, no more than 110 cm, no more than 100 cm, no more than 90 cm, no more than 80 cm, no more than 70 cm, no more than 60 cm, no more than 50 cm, no more than 40 cm, or no more than 30 cm, e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 100 cm, about 110 cm, about 120 cm, about 130 cm, about 140 cm, or about 150 cm).

In another aspect, the invention provides a method of implanting the gastrointestinal device of any of the preceding embodiments by securing the device to a surface proximal to or within the duodenum of a patient.

In a further aspect, the invention provides a method of treating a metabolic disorder by implanting the gastrointestinal device of any of the preceding by securing the device to a surface proximal to or within the duodenum of a patient. In some embodiments, the metabolic disorder is selected from the group consisting of type 2 diabetes, non-alcoholic steatohepatitis (NASH), non-alcoholic fatty liver disease (NAFLD), obesity, or a related comorbidity thereof.

BRIEF DESCRIPTION OF THE DRAWINGS

FIG. 1A shows a complete segmented gastrointestinal device. FIG. 1B shows a cylindrical non-erodible segment.

FIG. 2A shows a segmented sleeve made with diamond segments. FIG. 2B shows a diamond-shaped non-erodible segment.

DETAILED DESCRIPTION OF THE INVENTION

The present invention provides a gastrointestinal device for limiting contact of ingested material with a luminal wall along a segment of a patient's gastrointestinal tract (e.g., at the duodenum and/or upper jejunum). A device of the invention includes a sleeve (e.g., a gastric sleeve) having one or more segments. Each segment is connected by an erodible portion which, in some instances, erodes from the distal end of the sleeve to the proximal end of the sleeve. The invention also features methods of implanting the device of the invention within a patient. The invention further includes methods of treatment using the devices described herein, including methods of treating a metabolic disorder, such as type 2 diabetes, non-alcoholic steatohepatitis (NASH), non-alcoholic fatty liver disease (NAFLD), obesity, and related comorbities thereof by implanting a gastrointestinal device of the invention.

Definitions

As used herein, the term "incretin" refers to a compound that directly or indirectly stimulates insulin release, inhibits glucagon release, and reduces gastric emptying. For example, incretins stimulate an increase in the amount of insulin released from the pancreas when plasma glucose levels are elevated relative to normal after food consumption, thereby leading to a decrease in blood glucose levels. Specific examples of incretins include gastric inhibitory peptide (i.e., glucose-dependent insulinotropic polypeptide, or GIP) and glucagon-like peptide-1 (GLP-1), along with their analogs and derivatives.

As used herein, the term "sleeve" refers to a hollow, cylindrical liner that is open at both ends and adapted to extend at least into the duodenum. Partially digested food, or chyme, passing through the gastrointestinal tract passes through the interior of the sleeve.

As used herein, used herein, a "flanged" element or a "flange" refers to a projection that, when implanted in a subject, wholly or partially extends radially (i.e., in a direction having a radial component from a longitudinal axis of a pyloric orifice (e.g., between 90° and 180° outward from the longitudinal axis of the pyloric orifice)) and configured to attach a gastrointestinal device to a proximally oriented luminal surface (e.g., a proximal surface of the pyloric sphincter and/or an antral surface of the stomach).

As used herein, "conformable" refers to the ability to take the shape of the walls of a portion of the gastrointestinal tract upon insertion.

Unless otherwise specified, a longitudinal axis refers to the longitudinal axis of the gastrointestinal tract (i.e., the line running through the gastrointestinal lumen equidistant from the luminal walls). It will be understood that, due to the tortuosity of the gastrointestinal tract, the directionality of its longitudinal axis and associated radial coordinates will vary along its length. For cases in which the "longitudinal axis of the device" is referred to, it is explicitly referred to as such.

The orientation of any surface (e.g., a luminal surface, luminal wall, or device surface) is characterized herein according to the direction of its normal line (i.e., a vector originating at and projecting orthogonally outward from its surface). As used herein, the orientation of a gastrointestinal luminal surface is an average of any micro features and is therefore independent of, e.g., microvilli.

As used herein, the term "disintegrable" refers to any material which is capable being broken into one more segments.

As used herein, the term "degradable" refers to any material which is capable being dissolved under normal physiological conditions and passed through the body.

As used herein, the term "resorbable" refers to any material which is capable being absorbed into the body after dissolution under normal physiological conditions.

As used herein, the term "fluid" refers to a liquid or semisolid material, including any digested or partially digested liquid or semisolid material, for example, chyme and digestive secretions.

As used herein, the term "about" refers to +/−10% of a recited value.

As used herein, the terms "subject" and "patient" are used interchangeably and refer to any mammal (e.g., a human) having a gastrointestinal tract capable of containing of gastrointestinal implant of the invention. A patient who is being treated for a metabolic disorder, e.g., high blood sugar, diabetes (e.g., type 2 diabetes), obesity, NASH, NAFLD, or a related comorbidity thereof, may be one who has been diagnosed by a medical or veterinary practitioner as the case may be as having such a condition. Diagnosis may be performed by any suitable means. Patients of the invention may have been subjected to standard tests or may have been identified, without examination, as one at high risk of having or developing a metabolic disorder, e.g., type 2 diabetes, pre-diabetes, obesity, NASH, NAFLD, or a related comorbidity due to the presence of one or more risk factors, such as age, genetics, or family history.

As used herein, the term "comorbidity" or "related comorbidity" refers to one or more conditions, syndromes, diseases, or disorders that co-occur with metabolic disorders and can be either directly or indirectly linked to metabolic disorders. For example, metabolic disorder-related conditions may include pre-diabetes, type 2 diabetes, obesity, NAFLD, NASH, dyslipidemia, elevated serum/plasma LDL, elevated VLDL, elevated triglycerides, elevated cholesterol, plaque formation leading to narrowing or blockage of blood vessels, glucose intolerance, myocardial infarction, increased risk of hypertension/stroke, or coronary heart disease. As used herein, "diabetes mellitus type 2" or "type 2 diabetes" (also known as diabetes mellitus type 2, non-insulin-dependent diabetes (NIDDM), obesity-related diabetes, or adult-onset diabetes) refers to a metabolic disorder that is primarily characterized by insulin resistance, relative insulin deficiency, and hyperglycemia.

As used herein, the term "treatment" refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, the gastrointestinal implant is used to control metabolic disorders (e.g., type 2 diabetes, NASH, NAFLD, obesity, and related comorbidities). In some embodiments, removal of gastrointestinal implant is provided to delay development of a disease or to slow the progression of a disease.

Gastrointestinal Devices

The present invention features a gastrointestinal device designed to limit contact and transfer of material across luminal walls along a segment of the gastrointestinal tract (e.g., at the antrum, at the duodenum and/or upper jejunum). A device of the invention includes a sleeve (e.g., a gastric sleeve) having one or more segments connected by an erodible material. In some embodiments, the erosion of the sleeve occurs from the distal end of the sleeve to the proximal end of the sleeve.

Sleeves

Gastrointestinal sleeves suitable for adaptation for the presently disclosed gastrointestinal devices are known in the art and described, e.g., in U.S. Pat. Nos. 7,025,791, 7,608, 114, 7,695,446, 7,678,068, 7,122,058, 7,476,256, 7,815,589, 7,837,643, 8,057,420, 7,815,591, 7,771,382, and 7,766, 973, each of which is incorporated herein by reference.

In general, sleeves of the gastrointestinal device are thin-walled, collapsible, flexible, and floppy (i.e., they do not support the entirety of their weight, for example, if stood on end, they would buckle). Thus, sleeves can reduce or eliminate contact of fluid with walls of the intestine or digestive solutions secreted therefrom while transmitting natural peristaltic forces to propel the fluid through the intestines. After fluid from the stomach has passed through the sleeve, the sleeve may become thin and floppy, permitting the sleeve to conform (i.e., contour to the shape of) to the inner walls of the intestine. In some cases, the sleeve is substantially non-compliant and drapes away from the intestinal walls, thereby permitting pancreatic juices to flow unimpeded into the duodenum through the ampulla of vater.

The material the sleeve is formed form can be chosen such that the segments of the sleeve are substantially non-erodible, e.g., do not erode when in contact with digestive juices, in addition to the characteristics described above. Such properties can be found in a sleeve formed from a fluoropolymer, such as expanded polytetrafluoroethylene (ePTFE), or from a combination with another material. For example, one such combination includes an ePTFE layer of material combined with a different fluoropolymer layer, such as fluorinated ethylene-propylene (FEP). The combination of the FEP with ePTFE provides a low coefficient of friction while also being substantially non-permeable. In some embodiments, another material such as PTFE is applied to an ePTFE substrate using vapor deposition. Alternatively or in addition, the sleeve can be formed using polyolefin films, such as low density polyethylene (LDPE), high density polyethylene (HDPE), and polypropylene. Other materials suitable for use as part of a sleeve include cast polytetrafluoroethylene (e.g., TEFLON™), cast PTFE with FEP or perfluoroalkoxy (PFA) coating on a PTFE to minimize pin holes, extruded FEP and extruded PFA. These materials are solid and substantially non-porous, in contrast to ePTFE, which is generally porous. Alternatively or in addition, the sleeve may be made from a material that has microbial resistance, or the sleeve may have a surface coating of an antimicrobial agent. In some cases, the wall thickness of the sleeve is less than about 0.0025 inches (e.g., between 0.0003 and 0.0025 inches, e.g., from 0.0003 to 0.0010 inches, from 0.0010 to 0.0015 inches, from 0.0015 to 0.0020 inches, or from 0.0020 to 0.0025 inches, e.g., about 0.001 inches). The wall thickness of the sleeve can be uniform along its length or it can be variable.

Figure 1A:
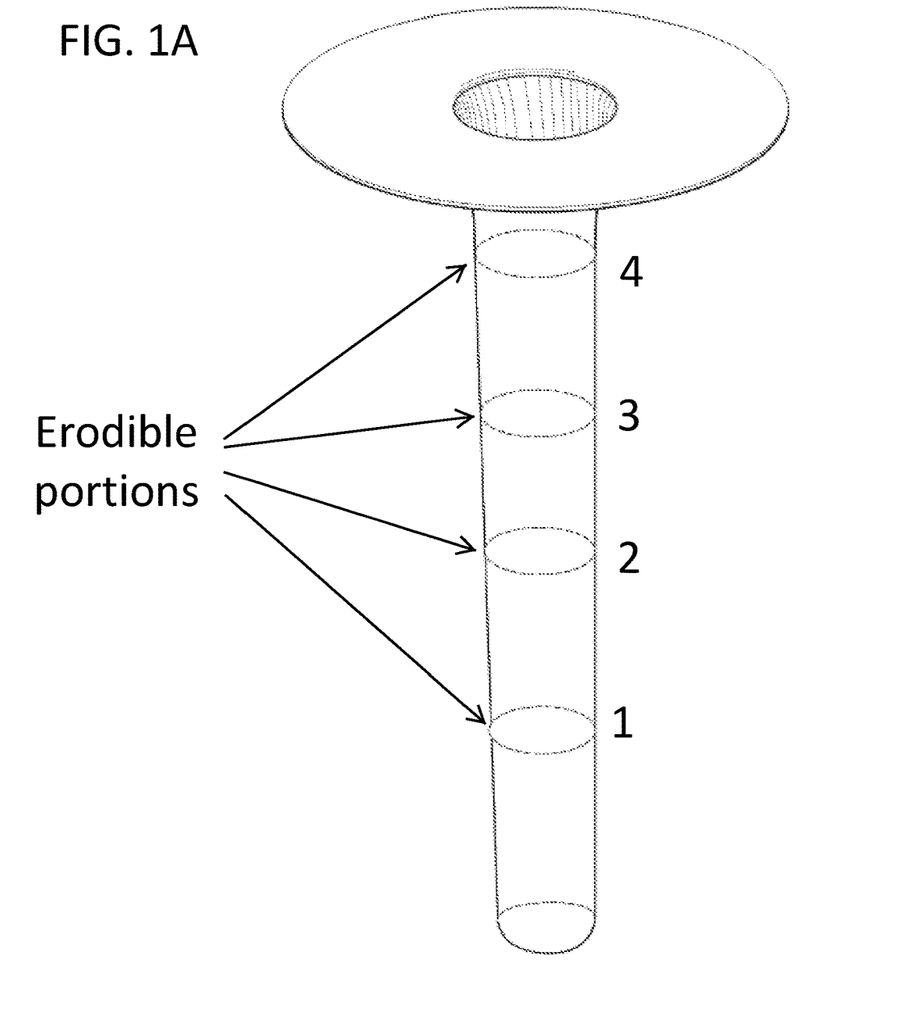
FIGS. 1A-1B are drawings of an embodiment of a flanged gastrointestinal device where the sleeve is made of four non-erodible cylindrical segments connected by erodible portions.
Figure 1B:
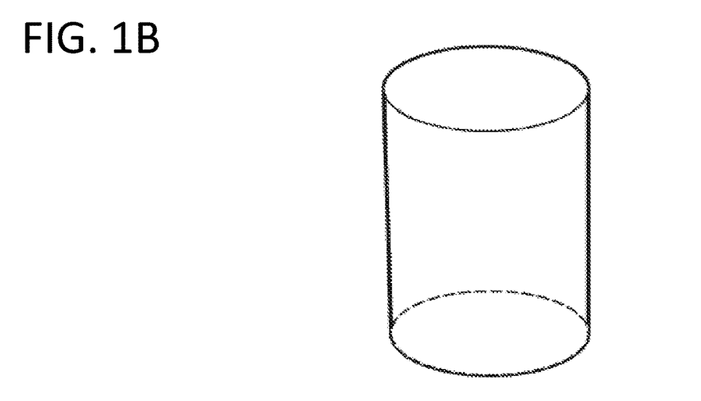

Sleeves can be divided into one more segments along the overall length of the sleeve as is shown in FIG. 1. Segmentation allows the sleeve to be safely and comfortably passed upon conclusion of the treatment period, e.g., without the need for endoscopic removal of the sleeve. The segments reduce or eliminate the possibility of the sleeve becoming tangled or causing a blockage to form within the gastrointestinal tract. The segments of the sleeve can be aligned along the longitudinal axis of the sleeve formed from the proximal end to the distal end of the sleeve. The number of segments of the sleeve, and/or the length of each segment may be determined by the overall length of the sleeve and the intended application or particular patient, e.g. depend on the patient's height, weight, or body mass index. In some cases, the number of segments of the sleeve is from 1 to 60 (e.g. from 2 to 55, from 3 to 50, from 4 to 45, from 5 to 40, from 6 to 35, from 7 to 30, from 8 to 25, from 9 to 20, from 10-15, or 12). In some cases, the segments of the sleeve may have a longitudinal dimension of about 1 cm to 30 cm (e.g., about 1 cm, about 2 cm, about 3 cm, about 4 cm, about 5 cm, about 6 cm, about 7 cm, about 8 cm, about 9 cm, about 10 cm, about 15 cm, about 20 cm, about 25 cm, or about 30 cm.

The one or more segments of the sleeve are connected together by one or more erodible portions such that when the portions erode, the segment(s) fall away from the remainder of the sleeve. Erodible materials are typically polymers including, but not limited to, poly(lactic acid) (PLA), poly (glycolic acid) (PGA), poly(L-lactic acid) (PLLA), poly-DL-lactide (PDLLA), poly-LD-lactide (PLDLA), diolamine, trimethylene carbonate, caprolactone, dioxanone, polydioxanone (PDO), and copolymers thereof, (e.g., poly(lactic-co-glycolic acid) (PLGA) or poly(L-lactide-DL-lactide) (PLDL)). Other erodible materials are known in the art. The erodible material may also be resorbable, e.g., absorbed within the gastrointestinal tract, after erosion. The segments of the sleeve are configured to erode in the distal-to-proximal direction. The erosion direction can be controlled by the composition of the erodible portion used to connect the segments together, the physical form of the erodible portion (e.g., shape, length, thickness, etc.), or the location of the erodible portions within the sleeve. For example, the segments of the sleeve can be connected by erodible portions of the same material, such as PGA, with the portions at the distal end of the sleeve being connected by a narrower or thinner portion such that the erosion of those portions has faster kinetics.

To control the erosion of the segments of the sleeve, the thickness of the one or more non-erodible portions connecting each segment may be modified. In some embodiments, the wall thickness of the one or more erodible portions is at least 5% less than the thickness of the non-erodible segments of the sleeve. In some embodiments, the wall thickness of the one or more erodible portions is at least 5% less (e.g., at least 5% less, at least 6% less, at least 7% less, at least 8% less, at least 9% less, at least 10% less, at least 11% less, at least 12% less, at least 13% less, at least 14% less, at least 15% less, at least 16% less, at least 17% less, at least 18% less, at least 19% less, at least 20% less, at least 30% less, at least 40% less, at least 50% less, at least 60% less, at least 70% less, at least 80% less, or at least 90% less) than the wall thickness if non-erodible segments of the sleeve. For example, the wall thickness of the erodible portions is less than about 0.000235 inches (e.g., between 0.00003 and 0.00025 inches, e.g., from 0.00003 to 0.00010 inches, from 0.00010 to 0.00015 inches, from 0.00015 to 0.00020 inches, or from 0.00020 to 0.00025 inches, e.g., about 0.0001 inches. The thickness of the erodible portions can be substantially uniform across the plurality of erodible portions. Alternatively, the erodible portions can be of varying thickness such that the erosion is controllable. For example, the thickness of the erodible portions connecting the proximal end of the sleeve may be thicker than those which connect sections at the distal end of the sleeve such that the thinner erodible portions erode prior to the thicker erodible portions.

Additionally or alternatively, each segment of the sleeve can be connected by a different erodible portion, e.g., such that the material connecting the distal segments of the sleeve erodes prior to those connecting the proximal portions of the sleeve.

The shape of the eroding portion can be of any suitable design, e.g., strips, straps, or bands. It will be appreciated by the skilled artisan that other shapes for joining materials are available. An exemplary shape for the eroding portions connecting non-erodible segments are strips. Strips are typically rectangular in shape. Each segment may be connected by a single strip having sufficient length to be secured around the circumference of the sleeve. Alternatively, each segment can be connected with multiple smaller strips spaced around the circumference of the sleeve. The erodible portions connecting the non-erodible segments may have a longitudinal width that, in some embodiments, may be no more than 10% that of the non-erodible segments of the sleeve. In some embodiments, the longitudinal width may be no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5%, no more than 6%, no more than 7%, no more than 8%, no more than 9%, or no more than 10% that of the non-erodible segments of the sleeve.

The erodible portions may connect the segments of the sleeve from either the interior of the sleeve, the exterior of the sleeve, or a combination thereof, e.g., by sandwiching abutting segments between an inner and outer layer of erodible material.

The erodible portions which connect the segments of the sleeves may also contain a therapeutic agent or nutritional supplement (e.g., a vitamin) for administration to the patient as the material erodes.

Gastrointestinal sleeves known in the art are typically cylindrical in shape, such as the example of a flanged gastrointestinal device shown in FIG. 1A. In one embodiment of a device of the invention, the segments can be of similar shape to that of the sleeve, e.g., cylindrical or annular, such as the segment shown in FIG. 1B. In some cases, each cylindrical segment may have a longitudinal dimension from about 1 cm to about 30 cm (e.g., from about 1 cm to about 2 cm, from about 2 cm to about 4 cm, from about 4 cm to about 6 cm, from about 6 cm to about 8 cm, from about 8 cm to about 10 cm, from about 10 cm to about 12 cm, from about 12 cm to about 14 cm, from about 14 cm to about 16 cm, from about 16 cm to about 18 cm, from about 18 cm to about 20 cm, from about 20 cm to about 22 cm, from about 22 cm to about 24 cm, from about 24 cm to about 26 cm, from about 26 cm to about 28 cm, from about 28 cm to about 30 cm).

Figure 2A:
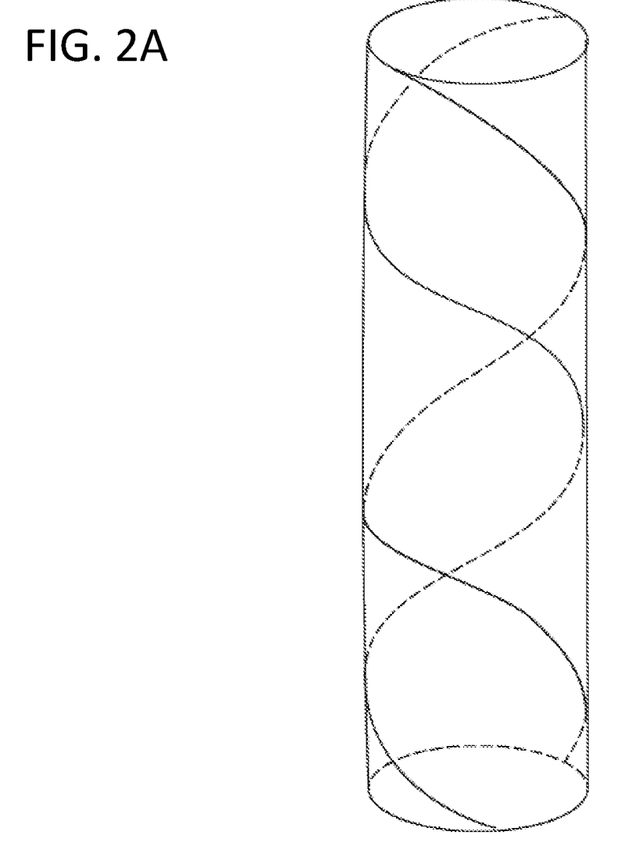
FIGS. 2A-2B are drawings of an embodiment of a gastrointestinal sleeve where the non-erodible portions are shaped to be connected together by diamond-shaped erodible portions.
Figure 2B:
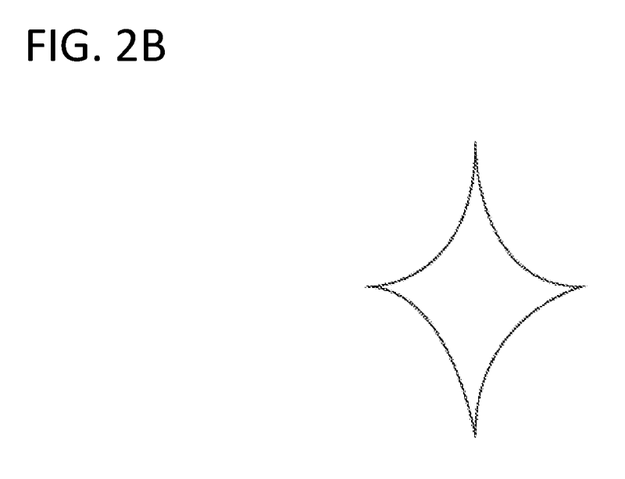

Additionally or alternatively, the segments of the sleeve may be of any suitable shape, e.g., polygonal, e.g. triangular, diamond, or hexagonal. FIG. 2A provides an example of a segmented sleeve with the segments having a diamond shape, with an example of a diamond shaped segment shown in FIG. 2B. It will be appreciated to the skilled artisan that any polygonal shape (and any combination of shapes) may be used for the segments of the sleeve. For example, when in a diamond shape, the lengths of the sides of the diamond may be of uniform length, e.g., a rhombus, or, alternatively, the length of the sides may be substantially non-uniform, e.g., a kite or parallelogram. In some cases, any longitudinal dimension of each polygonal segment (e.g., a minimum, maximum, or average longitudinal dimension) may be from about 1 cm to about 30 cm (e.g., from about 1 cm to about 2 cm, from about 2 cm to about 4 cm, from about 4 cm to about 6 cm, from about 6 cm to about 8 cm, from about 8 cm to about 10 cm, from about 10 cm to about 12 cm, from about 12 cm to about 14 cm, from about 14 cm to about 16 cm, from about 16 cm to about 18 cm, from about 18 cm to about 20 cm, from about 20 cm to about 22 cm, from about 22 cm to about 24 cm, from about 24 cm to about 26 cm, from about 26 cm to about 28 cm, from about 28 cm to about 30 cm).

In further embodiments, the sleeve may be connected with segments of identical shape. For example, each segment of the sleeve may be cylindrical, as shown in FIG. 1B. Alternatively, the sleeve can be made of segments with different shapes to control the erosion of the sleeve. For example, the distal end of the sleeve may be made of a shape which will erode with faster kinetics, such as a cylinder and the proximal end may be made of a shape which erodes more slowly, such as a polygon which has multiple erodible portions that must erode before the sleeve disintegrates (i.e., the segments fall away).

The erodible portions (1, 2, 3, 4) which connect the segments may be oriented along the separation boundaries defined by the shape of the segments. For example, annular segments may have the erodible portions, e.g., strips, oriented perpendicularly to the longitudinal axis formed by the proximal and distal ends of the sleeve. Other segment shapes, e.g., diamonds, may have the strips of erodible material connecting the segments of the sleeve running substantially non-perpendicularly to the longitudinal axis formed by the proximal and distal ends of the sleeve. The shape of the segment of the sleeve, and thus the erodible portions connecting the segments, may be a variable for controlling the erosion of the sleeve.

The length of the sleeve ranges from about 1 foot to about 5 feet (e.g., about 30 cm to about 150 cm). In some cases, the length of the sleeve is from 1 to 3 feet (e.g., 30 cm to 90 cm) from its proximal end (e.g., at a flange) to its distal end (e.g., below the ligament of Treitz). In some embodiments, the sleeve has a length of 12 inches, 13 inches, 14 inches, 15 inches, 16 inches, 17 inches, 18 inches, 19 inches, 20 inches, 21 inches, 22 inches, 23 inches, 24 inches, 25 inches, 26 inches, 27 inches, 28 inches, 29 inches, 30 inches, 31 inches, 32 inches, 33 inches, 34 inches, 35 inches, or 36 inches, e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm. The length of the sleeve can be selected to bypass the duodenum and a portion of the jejunum. The length may be increased to further decrease absorption by bypassing a longer section of the jejunum. Thus, the length of the sleeve is variable and may dependent on the patient's height, weight, or body mass index.

The sleeve can have a diameter similar to that of a normal subject's intestine, e.g., at the duodenum or jejunum. Additionally or alternatively, the diameter (e.g., maximum diameter) of the sleeve can be from 0.5 to 3 inches (e.g., from 1.0 to 2.0 inches, e.g., about 1.5 inches). By maximum diameter, it is meant the diameter when the sleeve is open and has a substantially circular cross-section.

In some cases, the device of invention provides eversion resistant sleeves. Eversion resistant sleeves refer to sleeves that resist proximal eversion (e.g., aberrant proximal movement through an anchoring system and/or pyloric orifice that may cause obstruction to the flow of fluid). Eversion resistant sleeves may be made from a thickening of the sleeve material, e.g., at a portion of the sleeve distal to the anchoring system, for example, as described in U.S. Pat. No. 7,766,973, which is herein incorporated by reference.

Methods

The invention further provides methods for delivering the gastrointestinal device, as well as methods of treating metabolic disorders, such as type 2 diabetes, non-alcoholic steatohepatitis (NASH), non-alcoholic fatty liver disease (NAFLD), obesity, and related comorbidities thereof.

Methods of Delivery

The invention further provides methods for implanting a gastrointestinal sleeve, such as those described herein. Methods of delivering gastrointestinal sleeves are known in the art and described, e.g., in U.S. Pat. Nos. 7,025,791, 7,678,068, 7,695,446, 7,837,643, 7,329,285, 8,870,806, 9,155,609, and 9,585,783, each of which is incorporated herein by reference.

The gastrointestinal device of the invention is configured to be delivered to a patient's gastrointestinal tract. In some embodiments, the device is configured to be delivered to a surface proximal to or within the duodenum of the patient (e.g., at the pylorus). Delivery of gastrointestinal sleeves is typically done endoscopically, with the sleeve being all or partially housed within a container at the distal end of the endoscope. The container may be capped at its distal end with an atraumatic cap to minimize the possibility of damaging the tissues of the gastrointestinal tract. The capped container may be guided to the pylorus or the duodenum using a guide wire whose length exceeds that of the endoscope. The endoscope contains an ejection mechanism (e.g., a plunger) where application of a distal force will release the device from the endoscope and into and/or through the pylorus to the duodenum.

The gastrointestinal device of the invention further includes a system by which to secure or anchor the sleeve within the gastrointestinal tract. Suitable anchor systems are known in the art. For example, the sleeve of the invention may include a friction-based anchor system where the most proximal segment has an anchor (e.g., a wave anchor) incorporated therein which exerts an outward radial force against a portion of the gastrointestinal tract (e.g., duodenum, e.g. duodenal bulb). Suitable anchor systems are known in the art and described, e.g., in U.S. Pat. Nos. 7,608,144, 8,137,301, 8,162,871, 9,155,609, 7,695,446, 7,678,068, 7,476,256, 7,682,330, 7,981,163, 8,834,405, 9,237,944, 7,815,589, 8,303,669, 8,628,583, 9,084,699, 7,976,488, and 8,425,451, each of which is incorporated herein by reference. After the distal portion of the sleeve is advanced to a desired location in the distal intestine, the wave anchor can be deployed from the container to secure the sleeve to the duodenal bulb. Another non-limiting example of an anchoring system for securing gastrointestinal devices of the invention is the incorporation of a flange to the proximal end of the sleeve, as described in U.S. Patent Application No. 62/289,100, incorporated herein by reference. The flange can be attached to a proximally oriented luminal surface (e.g., a pyloric sphincter or the antral surface of the stomach) by transmission of a distal force from an attachment element to the proximally oriented luminal surface. For example, the distal force can be directed (e.g., endoscopically) to an attachment element, such as a suture, staple, or anchor, to secure the flange to the luminal wall (e.g., by sequentially puncturing the flange and luminal wall, or by threading an eyelet or similar opening in the flange to access the luminal wall). The flange may further contain apertures (e.g., holes, slits, or slots) where the flange is connected to the attachment elements with a disintegrable tether. The flange, attachment elements and tether can be pre-assembled and housed within the container at the distal end of the endoscope, then deployed to allow the attachment elements to penetrate the pylorus once properly positioned, securing the gastrointestinal device. Additionally or alternatively, any suitable method of securing a film, liner, or membrane to a tissue, or combinations of anchoring systems thereof, can be used. For example, anchors useful for securing the sleeve of the present invention may include anchors that have pivoting or compressible retention elements, such as those disclosed in U.S. Pat. Nos. 9,572,565, 9,545,255, 8,740,940, 7,416,554, 7,361,180, and 7,736,379, each of which is incorporated herein by reference.

Methods of Treatment

Further provided herein are methods of treatment using a gastrointestinal device of the invention. In particular, the invention provides a method of treating a metabolic disorder by implanting a gastrointestinal device having a disintegrable sleeve described herein, e.g., by any suitable method of anchoring, e.g., by attaching the flange to a proximally oriented luminal surface proximal to the pyloric orifice (e.g., a proximal surface of the pyloric sphincter or the antrum of the stomach). Metabolic disorders treatable by such methods include type 2 diabetes, NASH, NAFLD, obesity, and related comorbidities thereof. Any of the gastrointestinal devices described above, delivered by any suitable method described above, can be used to treat a metabolic disorder.

Gastrointestinal devices of the invention have been shown to provide negative feedback within the enteric and/or nervous systems, reduced fat digestion, and reduced desire for food. Reduced fat digestion occurs because the sleeve delays the mixing of bile and pancreatic juices with chyme from the stomach until after the chyme leaves the sleeve. Reduced desire for food may occur because the sleeve reduces hormonal release from the duodenum. Additionally, providing poorly digested food to distal portions of the intestine, such as to the ileum, can trigger hormones that reduce appetite. Thus, such gastrointestinal devices can be used for treatment of various metabolic disorders (e.g., type 2 diabetes, NASH, NAFLD, and obesity) characterized by aberrant physiological response to ingested food, such as the incretin effect.

Placement of the gastrointestinal implant device may result in ingested food not digesting in a normal manner and modification of normal triggering of gut hormones. These hormones result in several physiology changes that impact hunger and digestion. Gut hormones that can be modified by devices of the invention include peptide YY (PYY), cholecystokinin (CCK) and ghrelin.

As under-digested food enters the ileum or distal part of the small intestine, PYY is released. PYY has been shown to have a direct effect on appetite, reducing it upon release. Undigested food in the ileum indicates that too much food has been ingested. Thus, dependent on the length of the sleeve, the gastrointestinal device can promote deposition of undigested or partially digested food to the distal bowel. Therefore, the placement of a sleeve in the intestine promotes the delivery of undigested food to the ileum, which in turn promotes the release of PYY and reduces appetite in humans.

The hormone CCK is released when food contacts the duodenum. CCK triggers the release of bile from the gallbladder. Therefore, placing a sleeve in the duodenum reduces the release of CCK and thus reduces bile output resulting in reduction in the digestion of food.

Some ghrelin is released when food contacts the duodenum. Ghrelin has been shown to be a factor in the control of appetite. Gastrointestinal devices of the invention can reduce ghrelin output and thereby reduce appetite due to the bypass of the duodenum.

Type 2 diabetes is a disease of obesity that occurs when patients cannot adequately use the insulin they produce. Usually, it is not that the patient cannot make enough insulin, but rather that the patient's body cannot effectively use the insulin produced. A particularly dangerous result of type 2 diabetes is that blood sugar spikes after a meal. This is called post-prandial hyperglycemia. This spike in blood glucose causes cardiovascular and microvascular damage. One class of drugs used to control post-prandial hyperglycemia is the alpha-glucosidase inhibitors. These work by reducing the breakdown and absorption of carbohydrates to sugars. The gastrointestinal device has a similar function because it reduces bile and delays the breakdown and absorption of the carbohydrates, which are normally readily absorbed in the duodenum, but are less likely to be absorbed in the jejunum and ileum. Therefore, type 2 diabetes can be controlled by placing a sleeve in the proximal intestine to delay the digestion of carbohydrates which reduces post-prandial hyperglycemia.

The gastrointestinal implant device can be used to reduce type 2 diabetes symptoms by bypassing all or a portion of the duodenum. Following gastric bypass surgery, patients commonly experience complete reversal of type 2 diabetes. While the exact mechanism of this remarkable effect is not understood, the clinical result is reported in a high percentage of cases. Since the gastrointestinal implant devices describe herein provides equivalent blockage of duodenal processes, a similar effect is elicited but without the trauma of surgery.

In the methods of using the gastrointestinal device described herein for treating diabetes, placement of the anchor within the stomach and/or duodenum allows the pylorus to operate normally. The length of the sleeve may be reduced to mimic the duodenum bypass. The sleeve may extends to just below the ligament of Treitz but may not extend further into the jejunum, thus allowing absorption to occur in the jejunum.

OTHER EMBODIMENTS

All publications, patents, and patent applications mentioned in this specification are herein incorporated by reference to the same extent as if each independent publication or patent application was specifically and individually indicated to be incorporated by reference. In the event of a conflicting definition between this and any reference incorporated herein, the definition provided herein applies.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims.

Other embodiments are within the claims.

What is claimed is:

1. A gastrointestinal device comprising a disintegrable sleeve comprising a proximal end and a distal end, the disintegrable sleeve configured to fit within the patient's duodenum and carry fluid from the proximal end to the distal end; wherein the disintegrable sleeve comprises a plurality of non-erodible segments connected by one or more erodible portions; wherein the one or more erodible portions and/or the plurality of non-erodible segments are polygonal; whereupon erosion of the one or more erodible portions, the plurality of non-erodible segments separate.

2. The gastrointestinal device of claim 1, wherein the plurality of non-erodible segments are aligned along a longitudinal axis.

3. The gastrointestinal device of claim 1, wherein a shape of the one or more erodible portions and/or the plurality of non-erodible segments varies in a distal-to-proximal direction and the one or more erodible portions are configured to erode in a distal-to-proximal direction.

4. The gastrointestinal device of claim 1, wherein the one or more erodible portions are strips.

5. The gastrointestinal device of claim 4, wherein the-strips run substantially non-perpendicularly to the longitudinally aligned non-erodible segments.

6. The gastrointestinal device of claim 1, wherein the one or more erodible portions have a longitudinal width that is no more than 10% that of the non-erodible segments of the sleeve.

7. The gastrointestinal device of claim 1, wherein the one or more erodible portions have a thickness that is at least 5% less than the non-erodible segments of the sleeve.

8. The gastrointestinal device of claim 1, wherein the erodible portions comprise a material selected from the group consisting of poly(lactic acid) (PLA), poly(glycolic acid) (PGA), diolamine, trimethylene carbonate, caprolactone, and copolymers thereof.

9. The gastrointestinal device of claim 8, wherein the erodible portions comprise PGA.

10. The gastrointestinal device of claim 1, wherein the non-erodible segments of the sleeve comprises a polymeric material.

11. The gastrointestinal device of claim 10, wherein the polymeric material is selected from the group consisting of polytetrafluoroethylene (PTFE), expanded polytetrafluoroethylene (ePTFE), fluorinated ethylene propylene (FEP), perfluoroalkoxy (PFA), ethylene tetrafluoroethylene (EFTE), and polyvinylidene fluoride (PVDF).

12. The gastrointestinal device of claim 11, wherein the polymeric material comprises PTFE.

13. The gastrointestinal device of claim 1, further comprising an anchoring system for securing the sleeve to a patient's gastrointestinal tract.

14. The gastrointestinal device of claim 1, wherein the sleeve contains an eversion-resistant element.

15. The gastrointestinal device of claim 1, wherein the sleeve is at least 30 cm in length.

16. A method of implanting the gastrointestinal device of claim 1, the method comprising securing the device to a surface proximal to or within the duodenum of a patient.

17. A method of treating a metabolic disorder, the method comprising implanting in a patient in need thereof the gastrointestinal device of claim 1, the method comprising securing the device to a surface proximal to or within the duodenum of a patient.

18. The gastrointestinal device of claim 1, wherein the one or more erodible portions and/or the plurality of non-erodible segments are triangular, hexagonal, rhomboidal, kite-shaped, parallelograms, or a combination thereof.

19. The gastrointestinal device of claim 1, wherein the one or more erodible portions and/or the plurality of non-erodible segments are diamond-shaped.

* * * * *

UNITED STATES PATENT AND TRADEMARK OFFICE
CERTIFICATE OF CORRECTION

| | |
|---|---|
| PATENT NO. | : 11,684,502 B2 |
| APPLICATION NO. | : 16/632787 |
| DATED | : June 27, 2023 |
| INVENTOR(S) | : Scott Schorer et al. |

It is certified that error appears in the above-identified patent and that said Letters Patent is hereby corrected as shown below:

In the Claims

Column 12, Claim 5, Lines 46-47, replace "the-strips" with --the strips--.

Signed and Sealed this
Twenty-fifth Day of June, 2024

Katherine Kelly Vidal
*Director of the United States Patent and Trademark Office*